US008721523B2

(12) United States Patent
Lee

(10) Patent No.: US 8,721,523 B2

(45) **Date of Patent: *May 13, 2014**

(54) MECHANIZED DILDO

(71) Applicant: Wing Pow International Corp., Chatsworth, CA (US)

(72) Inventor: Calvin Spencer Lee, Northridge, CA (US)

(73) Assignee: Wing Pow International Corp., Chatsworth, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/931,059

(22) Filed: Jun. 28, 2013

(65) Prior Publication Data

US 2013/0289344 A1 Oct. 31, 2013

Related U.S. Application Data

(63) Continuation of application No. 12/938,513, filed on Nov. 3, 2010, now Pat. No. 8,500,627, which is a continuation of application No. 11/971,797, filed on Jan. 9, 2008, now Pat. No. 7,828,717.

(60) Provisional application No. 60/978,315, filed on Oct. 8, 2007.

(51) Int. Cl.
*A61F 5/00* (2006.01)

(52) U.S. Cl.
USPC .......................................................... 600/38

(58) Field of Classification Search
CPC ....... A61H 19/34; A61H 19/40; A61H 19/44; A61H 19/50; A61H 19/30; A61H 19/32; A61H 23/00; A61H 2201/5071
USPC ............ 600/38–41; 601/72, 80, 97, 101–103, 601/112–114, 122, 125, 126, 129
See application file for complete search history.

(56) References Cited

U.S. PATENT DOCUMENTS

| | | | |
|---|---|---|---|
| 3,417,743 | A | 12/1968 | Carrera |
| 4,162,675 | A | 7/1979 | Kawada |
| 4,515,167 | A | 5/1985 | Hochman |

(Continued)

FOREIGN PATENT DOCUMENTS

| | | | |
|---|---|---|---|
| DE | 202004010534 | U1 | 5/2005 |
| DE | 102004033932 | A1 | 9/2005 |

(Continued)

OTHER PUBLICATIONS

European Search Report and European Search Opinion issued in European Application No. 10004175.5; Mar. 18, 2011.

(Continued)

*Primary Examiner* — Samuel Gilbert

(74) *Attorney, Agent, or Firm* — Sheldon Mak & Anderson PC

(57) ABSTRACT

A mechanized dildo, including a motor driven coaxial plurality of longitudinally spaced drive cams, and corresponding sets of passive cams that operate within an elastic phallic sleeve to locally cyclically expand a girth of the sleeve. Optional vibratory elements are positioned proximate a distal extremity of the sleeve, and in a laterally extending arm that is formed for clitoral stimulation. A battery powered control handle provides multiple operating modes and speeds.

23 Claims, 6 Drawing Sheets

(56) References Cited

U.S. PATENT DOCUMENTS

| | | | | |
|---|---|---|---|---|
| 4,779,615 | A | 10/1988 | Frazier | |
| 4,909,263 | A | 3/1990 | Norris | |
| 5,516,396 | A | 5/1996 | Maurer et al. | |
| 5,561,879 | A | 10/1996 | Everall | |
| 5,573,499 | A | 11/1996 | McAllister | |
| 5,601,529 | A | 2/1997 | Wollman | |
| 5,941,834 | A | 8/1999 | Skladnev | |
| 6,063,022 | A | 5/2000 | Ben-Haim | |
| 6,175,981 | B1 | 1/2001 | Lizama et al. | |
| 6,183,427 | B1 | 2/2001 | Ishii | |
| 6,350,230 | B1 | 2/2002 | Kontos | |
| 6,378,150 | B1 | 4/2002 | Minegishi et al. | |
| 6,616,621 | B1 | 9/2003 | Kohr | |
| 6,632,185 | B2 | 10/2003 | Chen | |
| 6,647,572 | B2 | 11/2003 | Lee | |
| 6,648,840 | B2 | 11/2003 | Cutler et al. | |
| 6,741,895 | B1 | 5/2004 | Gafni et al. | |
| 6,758,826 | B2 | 7/2004 | Luettgen et al. | |
| 6,902,525 | B1 | 6/2005 | Jewell | |
| 6,976,970 | B2 | 12/2005 | Siddhartha | |
| 7,081,087 | B2 | 7/2006 | Jannuzzi | |
| 7,104,950 | B2 | 9/2006 | Levy | |
| 7,122,015 | B2 | 10/2006 | Luettgen et al. | |
| 7,341,566 | B2 | 3/2008 | Nan | |
| 7,438,681 | B2 | 10/2008 | Kobashikawa et al. | |
| 7,503,892 | B2 | 3/2009 | Squicciarini | |
| 7,527,589 | B2 | 5/2009 | Squicciarini | |
| 7,534,203 | B2 * | 5/2009 | Gil | 600/38 |
| 7,559,886 | B2 | 7/2009 | Knyrim | |
| 7,608,037 | B2 | 10/2009 | Levy | |
| 7,828,717 | B2 * | 11/2010 | Lee | 600/38 |
| 8,500,627 | B2 * | 8/2013 | Lee | 600/38 |
| 2002/0029008 | A1 | 3/2002 | Pow Wong et al. | |
| 2002/0103415 | A1 | 8/2002 | Manska et al. | |
| 2003/0036678 | A1 | 2/2003 | Abbassi | |
| 2003/0083590 | A1 | 5/2003 | Hochman et al. | |
| 2004/0186344 | A1 | 9/2004 | Jannuzzi | |
| 2005/0012406 | A1 | 1/2005 | Moret | |
| 2005/0070827 | A1 | 3/2005 | Lee | |
| 2005/0113636 | A1 | 5/2005 | Tucker | |
| 2005/0113724 | A1 | 5/2005 | Wriggle | |
| 2005/0159685 | A1 | 7/2005 | Klein et al. | |
| 2005/0228219 | A1 | 10/2005 | Jewell | |
| 2006/0047181 | A1 | 3/2006 | Hsu | |
| 2006/0069329 | A1 | 3/2006 | Nan | |
| 2006/0084837 | A1 | 4/2006 | Klearman et al. | |
| 2006/0094992 | A1 | 5/2006 | Imboden et al. | |
| 2006/0143092 | A1 | 6/2006 | Gardos et al. | |
| 2007/0038019 | A1 | 2/2007 | Weng | |
| 2007/0149903 | A1 | 6/2007 | Nan | |
| 2007/0179336 | A1 | 8/2007 | Knyrim | |
| 2007/0179414 | A1 | 8/2007 | Imboden et al. | |
| 2008/0009775 | A1 | 1/2008 | Murison | |
| 2008/0065187 | A1 | 3/2008 | Squicciarini | |
| 2008/0082028 | A1 | 4/2008 | Blevins | |
| 2008/0119767 | A1 | 5/2008 | Berry et al. | |
| 2008/0139980 | A1 | 6/2008 | Fladl et al. | |
| 2008/0208083 | A1 | 8/2008 | Lin et al. | |
| 2009/0093856 | A1 | 4/2009 | Attila et al. | |
| 2009/0099413 | A1 | 4/2009 | Kobashikawa et al. | |
| 2009/0112055 | A1 | 4/2009 | Hyde et al. | |
| 2009/0171144 | A1 | 7/2009 | Squicciarini | |
| 2011/0218395 | A1 | 9/2011 | Stout | |

FOREIGN PATENT DOCUMENTS

| | | | |
|---|---|---|---|
| DE | 102005042092 | A1 | 10/2007 |
| DE | 202007012531 | U1 | 12/2007 |
| EP | 0472965 | A1 | 3/1992 |
| EP | 1720503 | B1 | 6/2007 |
| EP | 2047833 | B1 | 4/2009 |
| WO | 2005084605 | A1 | 9/2005 |
| WO | 2007041853 | A1 | 4/2007 |

OTHER PUBLICATIONS

European Search Report and European Search Opinion for European Application No. 08009779.3-1257.

Notice of Opposition from European Patent Office in Application No. 08009779.3, dated May 27, 2011 (1 page).

Opposition Papers Filed in European Patent Application No. 08009779.3, dated May 17, 2011, by Jörg Knyrim (10 pages).

* cited by examiner

MECHANIZED DILDO

CROSS REFERENCE TO RELATED APPLICATIONS

This application is a continuation of application Ser. No. 12/938,513, filed Nov. 3, 2010, which is a continuation of application Ser. No. 11/971,797, filed Jan. 9, 2008, which claims the benefit of Provisional Application Ser. No. 60/978,315, filed Oct. 8, 2007, all applications being incorporated herein in their entirety by this reference.

BACKGROUND

The present invention relates to sexual stimulation devices, and more particularly to a mechanized dildo.

Sexual stimulation devices of the prior art include dildos that have vibratory elements such as disclosed in U.S. Application Publication No. 2002/1013415 and International Publication No. WO 2007/041853. It is also known to provide arcuate deformation of a prosthetic device such as a dildo as disclosed in U.S. Application Publication No. 2006/0069329. However, it is believed that none of this class of devices of the prior art has proven entirely satisfactory, for a variety of reasons.

Thus there is a need for a sexual stimulation device in the form of a dildo that provides an improved form of stimulation and enhanced versatility as compared with existing devices.

SUMMARY

The present invention meets this need by providing a dildo that features an expandable girth, preferably a reciprocatingly expanding girth. In one aspect of the invention, the dildo includes a cam mechanism having a motor-driven shaft, a drive cam on and rotationally coupled to the shaft, a passive cam, and a guide structure for guiding the passive cam generally radially relative to the drive cam; a phallic sleeve preferably made of an elastic material; and a support structure supporting the sleeve in generally coaxial relation to the shaft and enclosing the passive cam in proximal relation to the sleeve, wherein the drive cam moves the passive cam to deflect a corresponding local region of the sleeve outwardly for expanding a girth of the sleeve. As the shaft rotates further, the cam recedes, and the elasticity of the deflected portion of the sleeve returns that portion of the sleeve to substantially its original unexpanded dimensions. Therefore the girth expansion is preferably reciprocating, as the shaft continues to rotate.

Preferably the passive cam is one of a plurality of passive cams in a set thereof, and the guide structure locates each passive cam of the set in a different radial orientation relative to the drive shaft for enhanced girth expansion. The drive cam can have a plurality of outwardly projecting lobes corresponding to the number of passive cams of the set, wherein the passive cams of the set operate in unison in response to rotation of the shaft. The drive cam can be one of a plurality of axially spaced drive cams, each drive cam having a corresponding set of passive cams associated therewith, and each drive cam can have the plurality of outwardly projecting lobes equal to the number of passive cams of the corresponding set, the passive cams of each set operating in unison in response to rotation of the shaft to produce corresponding girth enlargements. The sets of the passive cams can be angularly aligned, the drive cams also being angularly aligned for producing simultaneous girth enlargements. Alternatively, longitudinally alternating sets of the passive cams can be angularly offset, alternating ones of the drive cams being correspondingly angularly offset for producing differently oriented simultaneous girth enlargements. In another alternative, the sets of the passive cams are angularly aligned, and alternating ones of the drive cams are correspondingly angularly offset for producing alternating girth enlargements. In a further alternative, longitudinally alternating sets of the passive cams are angularly offset, and the drive cams are angularly aligned for producing differently oriented and alternating girth enlargements.

Preferably the dildo includes a motorized controller for operating the drive shaft. The controller can include a housing forming a handle for the dildo, a drive motor reduction-gear coupled to the drive shaft, and a main speed control for the motor. Preferably a vibrator mechanism is elastically supported by the phallic sleeve, the controller further including a vibrator speed control for the vibrator mechanism. The vibrator mechanism can be located in a head region of the phallic sleeve. The phallic sleeve can include a laterally extending arm portion for clitoral stimulation, the vibrator mechanism being located in the arm portion, a second vibrator mechanism being optionally located in the head region of the sleeve.

Preferably the controller is operative for changing speeds of the main motor and the vibration mechanism in response to a singular operator-controlled element. Alternatively, the controller includes separate operator-controlled elements for independent speed control of the main motor and the vibration mechanism.

DRAWINGS

These and other features, aspects, and advantages of the present invention will become better understood with reference to the following description, appended claims, and accompanying drawings, where:

DESCRIPTION

Figure 1:
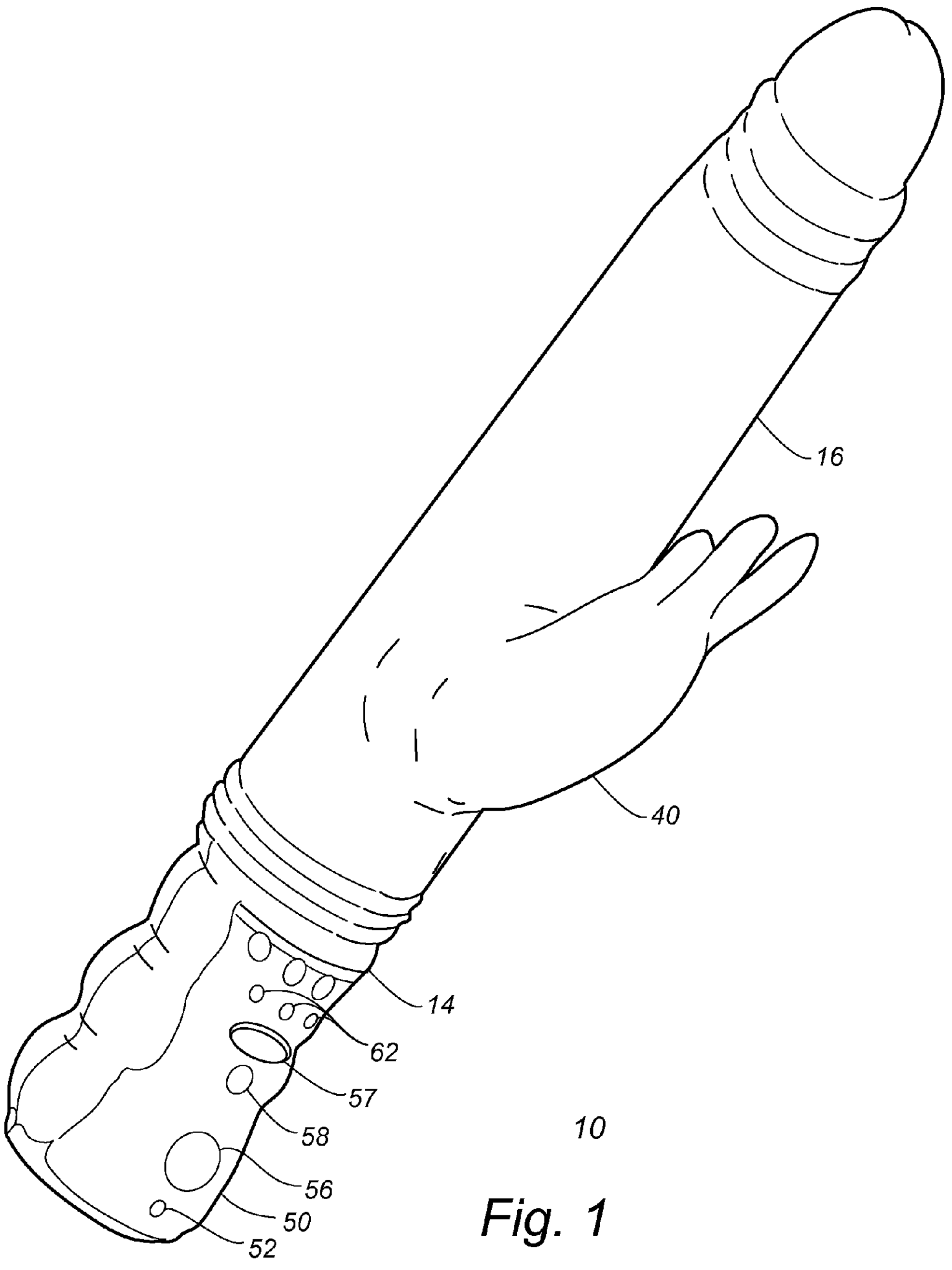
FIG. 1 is a perspective view of a mechanized dildo according to the present invention.

The present invention is directed to a mechanized dildo that is particularly effective in stimulating female genitalia. With reference to FIGS. 1-4 of the drawings, a mechanized dildo 10 includes a motorized cam assembly or mechanism 12, a control module 14, and a phallic sleeve 16 that encloses the cam mechanism. The cam mechanism 12 includes a main motor 18 that is operatively connected to a drive shaft 20 through a reduction gear train 22. A plurality of drive cams 24 (and individually designated 24A, 24B, and 24C) are rigidly supported on the shaft 20 for rotation therewith, each drive cam engaging a set 26 of passive cams 27 that are circumferentially equally spaced around the drive shaft, the passive cam sets being designated 26A, 26B, and 26C (numbered A,B,C in the direction of the shaft), the cams of each set being individually designated 27A, 27B, and 27C (numbered A,B,C around the shaft). The passive cams 27 are guided for generally radial motion by a plurality of guide rods 28 that engage corresponding slots 29 that are formed in the passive cams 27. A support member 30 holds a proximal end of each rod 28 in fixed relation to the motor 18, and a dome member 32 locates a distal end of each rod for holding the rods in parallel relation to the drive shaft 20. The phallic sleeve 16 contacts each of the passive cams 27, biasingly holding each cam 27 in sliding engagement with its associated drive cam 24. The phallic sleeve 16 is preferably made of an elastic material.

Each of the drive cams 24 has outwardly projecting and equally circumferentially spaced lobes 34 corresponding to the number of passive cams 27 of the corresponding set 26. Accordingly, and since the passive cams 27 of each set are also equally spaced, rotation of the drive shaft 20 produces synchronous radial reciprocation of the passive cams 27 of each particular set, correspondingly producing outward local elastic radial expansion and contraction of the sleeve 16 proximate each of the passive cams of that set, thereby increasing and decreasing a local girth of the sleeve 16 in a region thereof associated with the set 26 of passive cams 27. The elastic tension within the phallic sleeve moves the passive cams inwardly as the respective lobes rotate beyond maximum passive cam displacement.

Preferably the phallic sleeve has a nominal diameter of from approximately 1.2 inches (30 mm) to approximately 2.0 inches (50 mm), and a nominal length of from approximately 5 inches (127 mm) to approximately 9 inches (228 mm), and the girth expansion can be from approximately 0.12 inch (3.1 mm) up to approximately 0.79 inch (20 mm), which corresponds to an increase in diameter of from approximately 0.04 inch (1 mm) to approximately 0.39 inch (10 mm). Of course, other dimensions are possible, depending on user preference.

Figure 2:
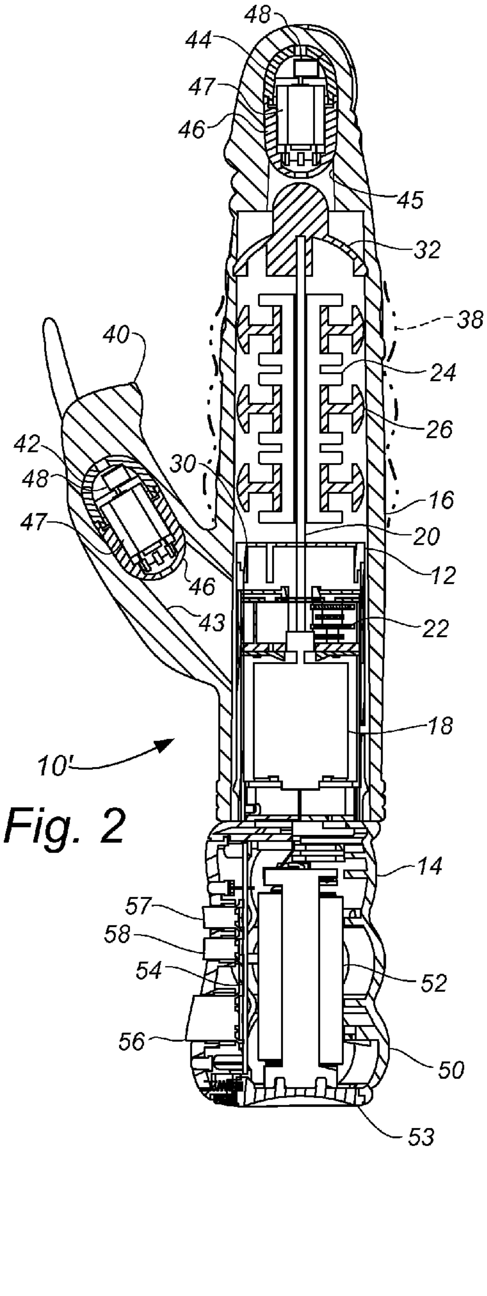
FIG. 2 is a lateral sectional view of the mechanized dildo of FIG. 1.
Figure 8:
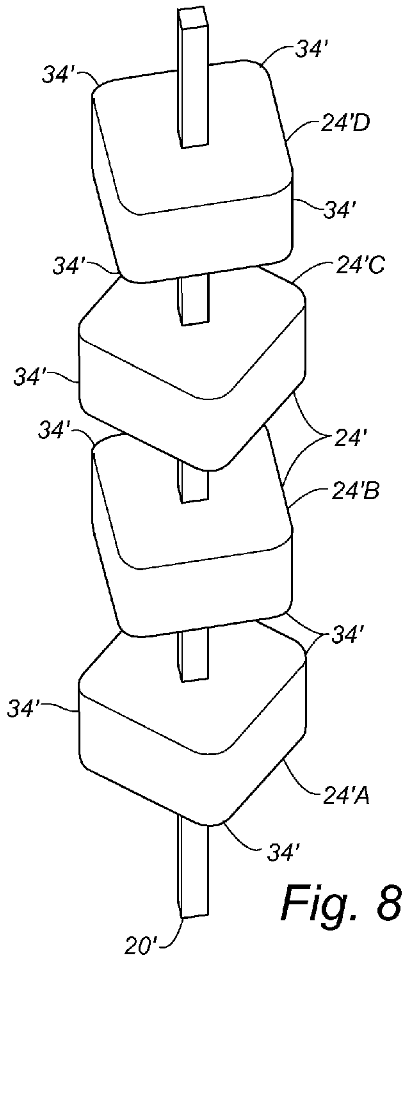
FIG. 8 is a perspective view as in FIG. 3, showing drive cams and shaft of the mechanized dildo of FIG. 5.
Figure 3:
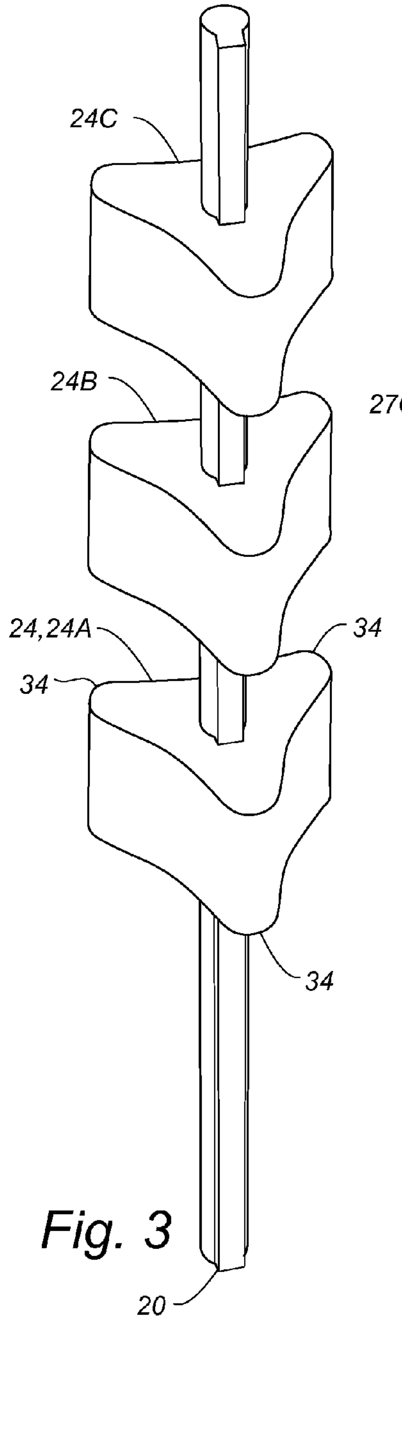
FIG. 3 is a perspective view showing a drive shaft and drive cams of the mechanized dildo of FIG. 1.
Figure 4:
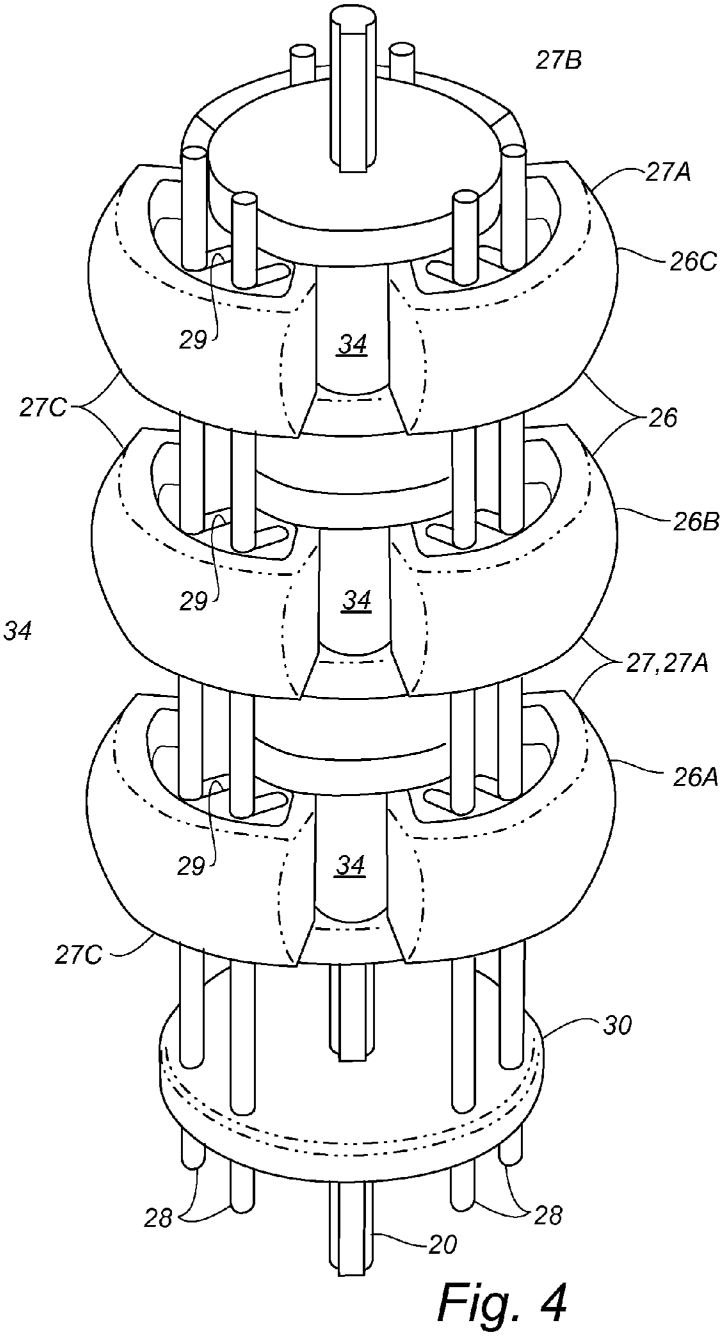
FIG. 4 is a perspective view as in FIG. 3, showing the drive shaft and drive cams assembled in a cam mechanism of the dildo.
Figure 5:
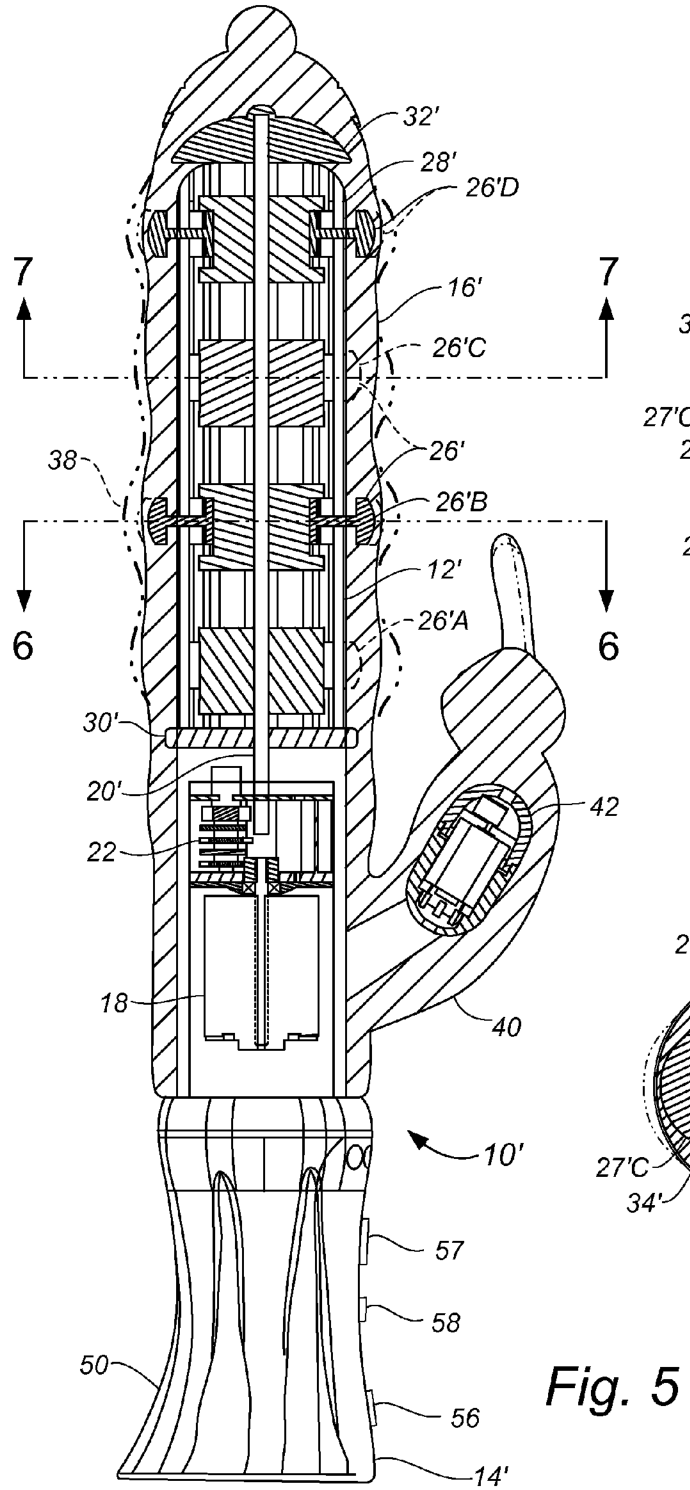
FIG. 5 is a sectional view as in FIG. 2, showing an alternative configuration of the mechanized dildo.
Figure 7:
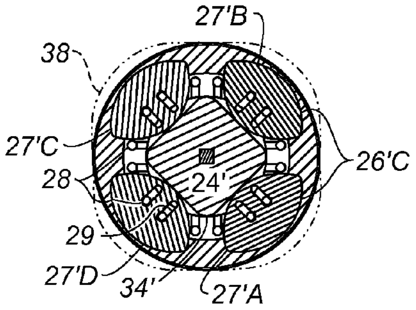
FIG. 7 is an axial sectional view on line 7-7 of FIG. 5.
Figure 6:
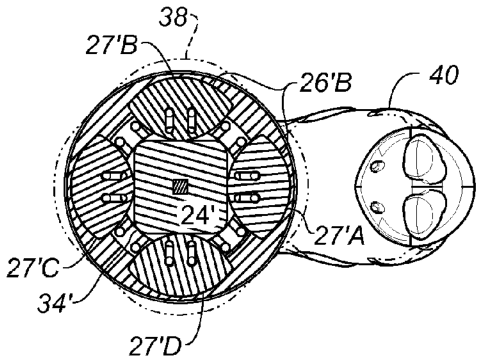
FIG. 6 is an axial sectional view on line 6-6 of FIG. 5.
Figure 9:
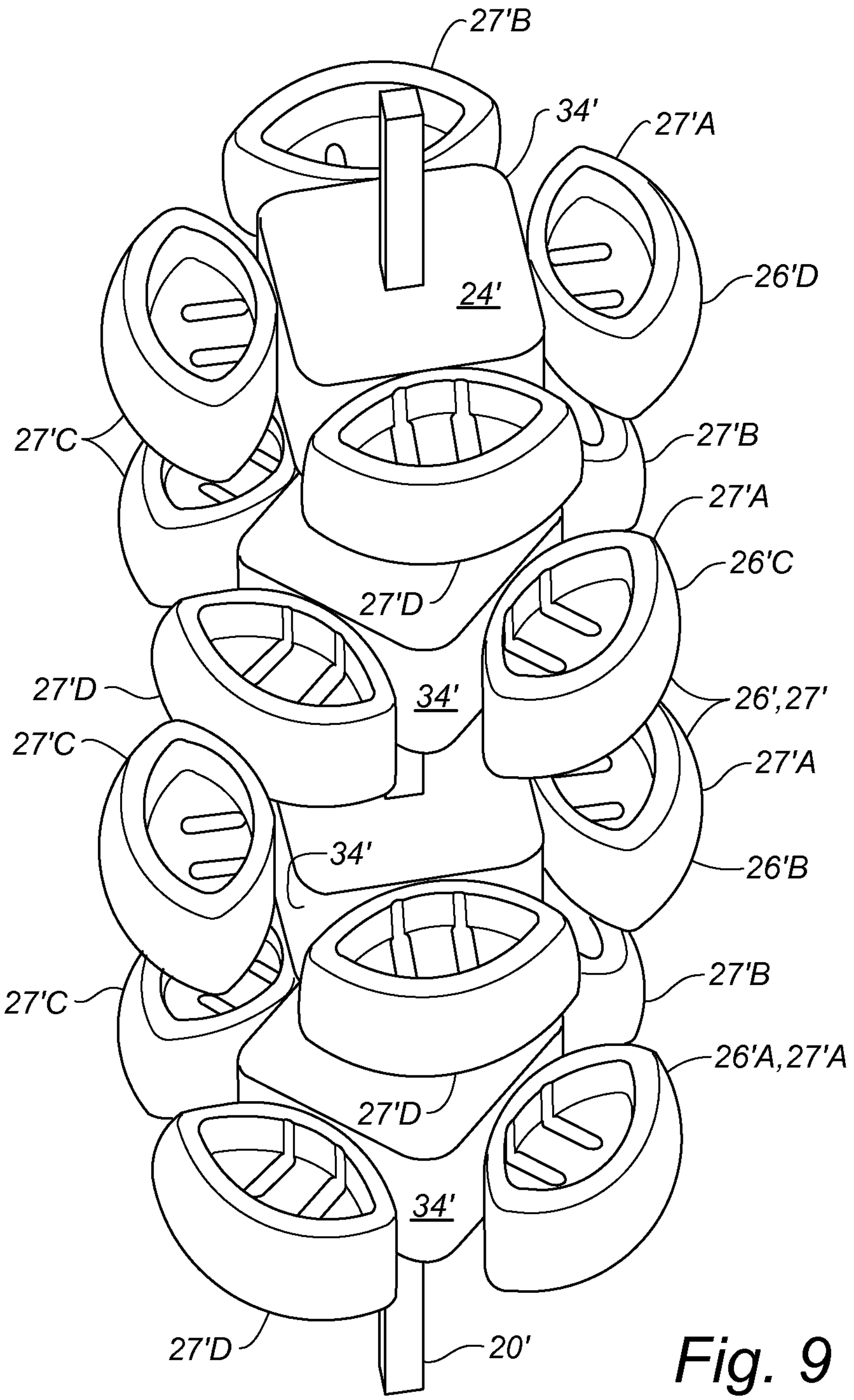
FIG. 9 is a perspective view as in FIG. 6, showing the drive cams and shaft together with associated passive cams of the dildo of FIG. 5.
Figure 10:
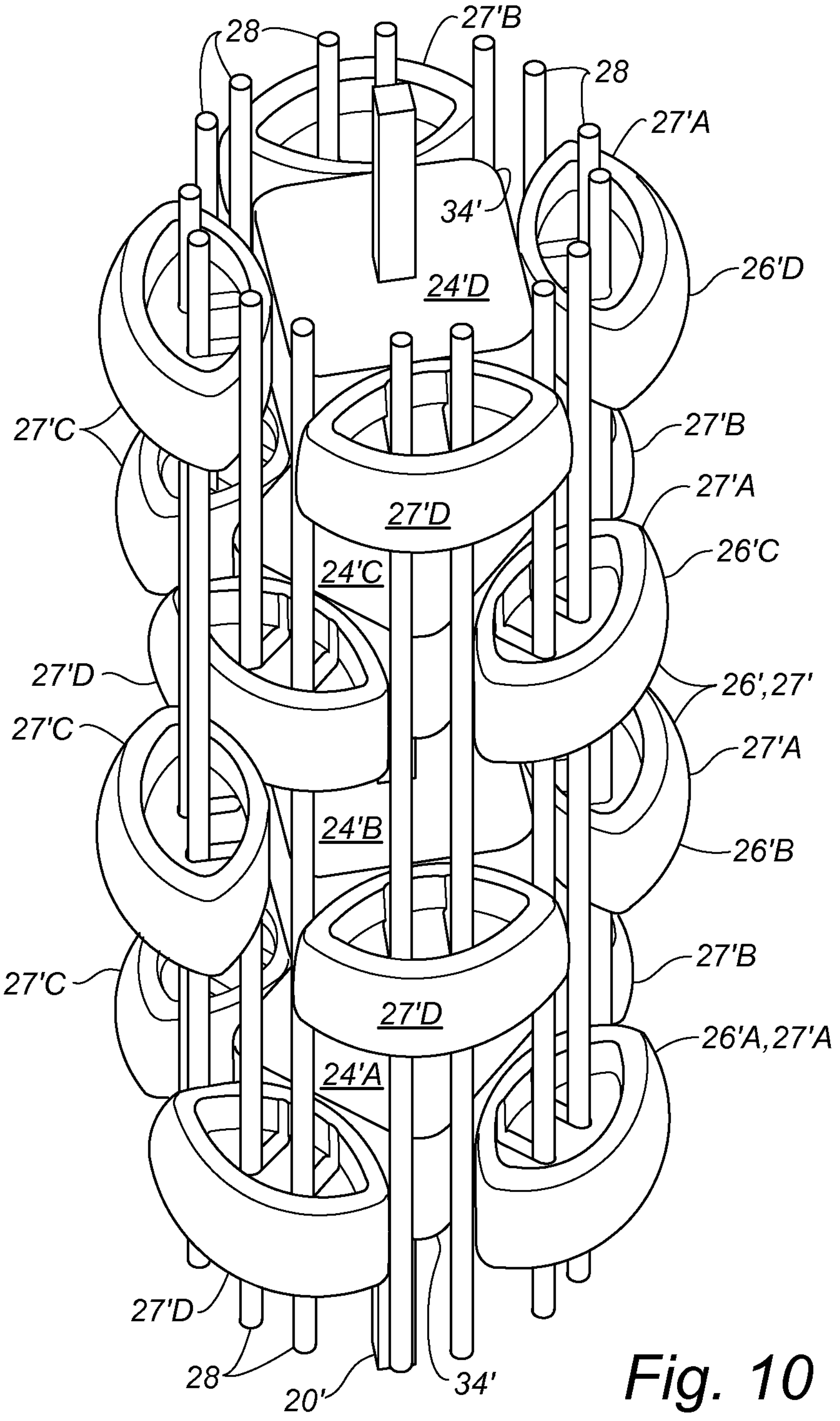
FIG. 10 is a perspective view as in FIG. 7, showing the cams and drive shaft assembled in a cam mechanism of the dildo of FIG. 5.

In the exemplary embodiment shown in FIGS. 1-4, the drive cams 24A, 24B, and 24C are “in-phase” on the drive shaft 20 and the passive cams of each set 26A, 26B, and 26C are also “in-phase” relative to the other sets; thus the expansion and contraction of the respective local girths is also both in unison and in phase, the sleeve 16 expanding from a relatively relaxed condition shown by solid lines to an expanded condition shown by broken lines as indicated, for example, at 38 in FIG. 2.

As also shown in FIGS. 1 and 2, the dildo 10 has an arm member 40 that is formed as a lateral extension of the phallic sleeve 16 in a shape and dimension preferably facilitating contact with the clitoris of a user of the dildo, a first vibrator 42 being locatingly supported within an arm cavity 43 of the arm member 40. As further shown in FIG. 2, a second vibrator 44 is locatingly supported within a head cavity 45 proximate a distal end of the phallic sleeve 16. Each of the vibrators 42 and 44 preferably includes a two-piece housing 46 enclosing a vibrator motor 47 that rotates an eccentric weight member 48 in a conventional manner and as further described below.

The control module 14 includes a control housing 50 that serves as a handle of the dildo 10 and which also encloses a battery pack 52 (which is retained by a removable cap 53) and a circuit board 54, there being appropriate wiring or other conductors (not shown) between the battery pack 52, the circuit board 54, the main motor 18, and the vibrator motors 47. In the configuration shown in FIGS. 1-4, the control module has a power switch actuator 56, a mode switch actuator 57, and a speed switch actuator 58, each actuator protruding the housing 50 for operation by a user and having an associated switch (not shown) on the circuit board 54. The circuit board 54 has a power indicator 60 and a plurality of intensity indicators 62 that project through the housing for facilitating operation by the user. The mode switch actuator 57 sequentially selects a plurality of vibration and throbbing (reciprocating girth expansion) combinations, by selectively activating the main motor 18 and/or the vibrator motors 47 in accordance with methods known to those skilled in the art. The speed switch actuator sequentially selects different speeds of both vibration and throbbing, also in accordance with methods known to those skilled in the art.

Regarding the throbbing, or reciprocating girth expansion, a preferred range of throbbing rates is between approximately 50 to approximately 180 times per minute. Preferred vibration rates are from approximately 20 per second to approximately 120 per second.

Suitable materials for the drive shaft 20 and the guide rods 28 include hardened steel; suitable materials for the support member 30, the dome member 32, the vibrator housings 46, the control housing 50, and the switch actuators 56, 57, and 58 include ABS. Suitable materials for the drive cams 24 and the passive cams 27 include POM and other substantially rigid plastics; suitable materials for the battery module include polypropylene; and suitable materials for the phallic sleeve include elastic plastic materials such as TPE. A suitable battery complement is four type AAA alkaline batteries.

With further reference to FIGS. 5-10, an alternative configuration of the mechanical dildo, designated 10', includes counterparts of the cam mechanism, designated 12', the control module, designated 14', the phallic sleeve, designated 16', the main motor 18, and the gear train 22. There are four of the drive cams, designated 24' (and individually 24A', 24B', 24C', and 24D'), and correspondingly four sets of four equally spaced passive cams, designated 26' (individually 26A', 26B', 26C', and 26D'), the cams of each set being designated 27'. A drive shaft 20' and a plurality of guide rods 28' are lengthened counterparts of the drive shaft 20 and guide rods 28 of the configuration of FIGS. 1-4, for accommodating the extra drive cam 24D' and passive cam set 26D'. A support member 30', and dome member 32' are counterparts of the above-described support member 30 and dome member 32, configured for supporting additional guide rods associated with the extra passive cam 27' of each set 26'.

As further shown in FIGS. 6-10, each of the drive cams 24' has four equally spaced drive cam lobes, designated 34', such that the passive cams 27' of each set 26' move in unison with the other passive cams of that set. Alternating pairs of the drive cams 24' are 45 degrees out of phase on the drive shaft 20'. More particularly, the drive cams 24A' and 24C' are in-phase with each other and 45 degrees out of phase with the drive cams 24B' and 24D'. Also in the same manner, alternating sets of the passive cams 27' are out of phase with each other. Accordingly, all of the passive cams 27' move in unison in response to rotation of the drive shaft 20'; however, the local girth expansions that result are staggered at 45 degrees between regions of the sleeve 16' associated with adjacent sets 26' of the passive cams 27'. It will be understood that aligned mounting of the drive cams 24' in combination with the staggered arrangement of the passive cams 27' will produce alternating expansion and contraction of the phallic sleeve 16' proximate adjacent pairs of passive cam sets 26'. For example, during simultaneous expansion proximate the passive cam sets 26'A and 26'C there is corresponding contraction of the sleeve proximate the other passive cam sets 26'B and 26'D. Continued rotation of the drive shaft 20' produces expansion proximate the passive cam sets 26'B and 26'D and corresponding contraction proximate the cam sets 26'A and 26'C. Conversely, the staggered configuration of drive cams 24' shown in FIG. 8, in combination with an aligned configuration of passive cams (corresponding to the arrangement shown in FIG. 4) also produces simultaneous expansion and contraction proximate alternating sets of the passive cams, but with the local expansions being axially aligned as in the configuration of FIGS. 1-4. In configurations having one or the other of the of the drigve cams and the passive cam sets out of phase, the rotation of the drive shaft 20' causes the girth of the dildo to expand and contract in different lengthwise portions corresponding to the out-of-phase cam sets along the length of the dildo.

Although the present invention has been described in considerable detail with reference to certain preferred versions thereof, other versions are possible. For example, any number of drive cams and passive cam sets, and any number of passive cams per set are contemplated within the scope of the present invention. Also, the number of lobes on each cam can be different than the number of passive cams operated thereby, although a multiple or submultiple of that number is preferred, the equal numbers (three and four) described above being most preferred. Further, the drive cams can be supported other than rigidly on the drive shaft, such as with back-lash, or with an elastic connection. Moreover, a single cam member can form plural drive cams. Therefore, the spirit and scope of the appended claims should not necessarily be limited to the description of the preferred versions contained herein.

What is claimed is:

1. A dildo comprising an elastic phallic sleeve enclosing an expanding mechanism, the expanding mechanism being in contact with the sleeve, the expanding mechanism being operative for reciprocatingly expanding the diameter of the sleeve at plural longitudinally spaced apart locations along a longitudinal axis of the sleeve, axially adjacent ones of the plural locations expanding in phase and in unison.

2. The dildo of claim 1, wherein the expanding mechanism comprises plural expanding elements, an expanding element fixedly located at each of the plural locations.

3. The dildo of claim 2, further comprising a shaft supporting the expanding elements.

4. The dildo of claim 1, wherein there is less expansion in regions between the locations.

5. The dildo of claim 1 wherein the expansion in axially adjacent locations occurs in the same circumferential regions of the respective adjacent locations.

6. A dildo comprising an elastic phallic sleeve enclosing an expanding mechanism, the expanding mechanism being in contact with the sleeve, the expanding mechanism being operative for reciprocatingly expanding the diameter of the sleeve at plural longitudinally spaced apart locations along a longitudinal axis of the sleeve, axially adjacent ones of the plural locations expanding in phase and in unison, wherein the expanding mechanism is operative to cause expansion at diametrically opposed regions of the sleeve at the plural locations.

7. The dildo of claim 6, further comprising a motor for expanding the diameter of the sleeve.

8. The dildo of claim 7, further comprising a motor controller for controlling the motor.

9. The dildo of claim 7, further comprising:

(a) a housing forming a handle for the dildo;

(b) a battery pack in the housing;

(c) a power switch supported by the housing; and (d) a speed control for the motor, the speed control being supported by the housing.

10. The dildo of claim 6, wherein the sleeve comprises a laterally extending arm portion for clitoral stimulation, and further comprising a vibrator mechanism elastically supported by the sleeve, the vibrator mechanism being located in the arm portion.

11. The dildo of claim 10, further comprising a vibrator speed control for the vibrator mechanism.

12. The dildo of claim 11 comprising a controller operative for changing speeds of the vibration mechanism in response to a singular operator-controlled element.

13. The dildo of claim 6 wherein the expanding mechanism is powered for cyclically expanding the diameter of the sleeve.

14. The dildo of claim 6, wherein the expanding mechanism is powered for reciprocatingly expanding the diameter of the sleeve.

15. The dildo of claim 6, wherein the expanding mechanism expands the girth at the plural locations by approximately 0.12 to approximately 0.79 inches.

16. The dildo of claim 6, wherein the expanding mechanism expands the diameter at the plural locations by approximately 0.04 inches to approximately 0.39 inches.

17. The dildo of claim 6, wherein there are three locations where the diameter is expanded.

18. The dildo of claim 6, further comprising a central shaft supporting the expanding mechanism.

19. The dildo of claim 6, wherein the expanding mechanism comprises plural expanding elements, an expanding element fixedly located at each of the plural locations.

20. The dildo of claim 6, wherein there is less expansion in regions between the locations.

21. The dildo of claim 6 wherein the expansion in axially adjacent locations occurs in the same circumferential regions of the respective adjacent locations.

22. A dildo comprising an elastic phallic sleeve enclosing an expanding mechanism, the expanding mechanism comprising expansion elements against and in contact with the sleeve, the expanding mechanism being operative for reciprocatingly expanding the diameter of the sleeve at plural longitudinally spaced apart locations along a longitudinal axis of the sleeve, an expansion element at each location, axially adjacent ones of the plural locations expanding in phase and in unison with less expansion in regions between the locations.

23. A dildo comprising:

(a) an elastic phallic sleeve, wherein the sleeve is made of an elastic material;

(b) an expanding mechanism enclosed by the sleeve, the expanding mechanism comprising a plurality of expansion elements, an expansion element being located at each of the plural locations, the expansion elements being against and in contact with the sleeve, the expanding mechanism being operative for reciprocatingly and cyclically expanding the diameter of the sleeve at longitudinally spaced apart plural locations along a longitudinal axis of the sleeve, axially adjacent ones of the plural locations expanding in phase and in unison, wherein the expanding mechanism expands the diameter at diametrically opposed regions of each location by approximately 0.04 inches to approximately 0.39 inches;

(c) a laterally extending arm portion elastically supported by the sleeve, the arm portion comprising a vibrator mechanism, the vibrator mechanism comprising a vibrator speed control; and (d) a motor for expanding the diameter of the sleeve, the motor comprising:
(i) a motor controller for controlling the motor;
(ii) a housing forming a handle for the dildo;
(iii) a battery pack in the housing;
(iv) a removable cap for providing access to the battery pack;
(v) a power switch supported by the housing; and
(vi) a speed control for the motor, the speed control being supported by the housing.

* * * * *